United States Patent
Lamberti et al.

(10) Patent No.: US 9,895,465 B2
(45) Date of Patent: Feb. 20, 2018

(54) ABSORBABLE COMPOSITIONS AND METHODS FOR THEIR USE IN HEMOSTASIS

(71) Applicant: Pioneer Surgical Technology, Inc., Marquette, MI (US)

(72) Inventors: Francis Vincent Lamberti, Cary, NC (US); Barbara Sage, Greenville, NC (US)

(73) Assignee: Pioneer Surgical Technology, Inc., Marquette, MI (US)

(*) Notice: Subject to any disclaimer, the term of this patent is extended or adjusted under 35 U.S.C. 154(b) by 61 days.

(21) Appl. No.: 14/656,032

(22) Filed: Mar. 12, 2015

(65) Prior Publication Data
US 2015/0258239 A1    Sep. 17, 2015

Related U.S. Application Data

(60) Provisional application No. 61/951,859, filed on Mar. 12, 2014.

(51) Int. Cl.
*A61L 24/00* (2006.01)

(52) U.S. Cl.
CPC ....... *A61L 24/0015* (2013.01); *A61L 24/0042* (2013.01); *A61L 24/0084* (2013.01); *A61L 2300/402* (2013.01); *A61L 2400/04* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,439,420 A * | 3/1984 | Mattei | A61K 31/20 424/78.38 |
| 4,568,536 A | 2/1986 | Kronenthal et al. | |
| 4,650,665 A | 3/1987 | Kronenthal et al. | |
| RE39,587 E * | 4/2007 | Gertzman et al. | A61L 27/52 424/423 |
| 7,357,789 B2 * | 4/2008 | Bills | A61O 5/062 604/187 |
| 7,955,616 B2 | 6/2011 | Kronenthal | |
| 7,989,000 B2 | 8/2011 | Kronenthal | |
| 2002/0034531 A1 * | 3/2002 | Clokie | A61L 27/227 424/422 |
| 2002/0192263 A1 * | 12/2002 | Merboth | A61K 6/08 424/426 |
| 2005/0065214 A1 * | 3/2005 | Kronenthal | A61K 31/19 514/557 |
| 2005/0214331 A1 * | 9/2005 | Levy | A61K 9/4808 424/400 |
| 2007/0078095 A1 * | 4/2007 | Phares | C07C 59/70 514/762 |
| 2011/0021964 A1 | 1/2011 | Larsen et al. | |
| 2011/0028970 A1 | 2/2011 | Woloszko et al. | |
| 2011/0201553 A1 | 8/2011 | Johansson et al. | |
| 2012/0027817 A1 | 2/2012 | Kronenthal | |
| 2012/0189671 A1 | 7/2012 | Kronenthal | |
| 2012/0207847 A1 * | 8/2012 | Butler | A61L 27/26 424/549 |
| 2012/0258159 A1 | 10/2012 | Vogt | |

FOREIGN PATENT DOCUMENTS

WO    WO 2012/123728 A2    9/2012

* cited by examiner

*Primary Examiner* — Jennifer A Berrios
(74) *Attorney, Agent, or Firm* — Green, Griffith & Borg-Breen LLP

(57) ABSTRACT

The present invention is direct to a body-absorbable, mechanically hemostatic composition comprising a solid poloxamer having an average molecular weight of about 7,000 g/mol to about 15,000 g/mol, a high molecular weight dextran, optionally a fatty acid salt, and water, and a method for mechanically controlling the bleeding of bone comprising applying an effective amount of the composition to the affected area.

2 Claims, No Drawings

ABSORBABLE COMPOSITIONS AND METHODS FOR THEIR USE IN HEMOSTASIS

CROSS-REFERENCE TO RELATED APPLICATIONS

This application claims the benefit of U.S. Provisional Patent Application No. 61/951,859, which was filed on Mar. 12, 2014, and which is incorporated by reference in its entirety herein.

BACKGROUND OF THE INVENTION

The invention relates to an absorbable implantable composition and method of use for surgical control of osseous hemorrhage and improvement of healing of osseous defects.

Cancellous and cortical bone contains relatively vascular tissues that bleed when their vasculature is disrupted. Thus, when bone is surgically incised or fractured traumatically, e.g., in open or compound fractures, there are at least two major issues which must be medically resolved. The first of these is the occurrence of osseous hemorrhage. When osseous hemorrhage ensues, it must be stopped or effectively controlled (hemostasis) to prevent adverse surgical consequences. The second issue is that of bone growth to promote healing (osteogenesis) of the traumatized bone. Common procedures in which bone is surgically cut include open-heart surgery involving the splitting of the sternum, orthopedic and spinal surgery including hip implants, neurosurgery involving spine or cranial incisions, amputations, trauma treatment, and many other procedures.

At the present time, bone hemostasis is achieved by one or more of (i) manually impregnating the bleeding surface with commercially available, non-absorbable "bone wax" to achieve mechanical control of bleeding, (ii) applying one or more hemostatic agents or sealants such as oxidized cellulose, microcrystalline collagen, human thrombin, and human fibrinogen, to enhance coagulation at the bleeding site, and (iii) electrocautery. None of these techniques promotes osteogenesis to any significant extent. In addition to the unmet need for an effective, rapidly absorbable bone hemostatic material, there is also a surgical need for materials to fill bone defect voids and promote healing in such cavities. A variety of paste-like materials, presently available to the surgeon for this purpose, most commonly are based upon coarsely powdered, demineralized allogeneic bone, suspended in a suitable, biocompatible vehicle. These compositions are designed for inducing osteogenesis and healing in the defect but, because of their consistency, non-cohesiveness and other physical attributes of their composition, they do not reliably adhere to injured bone and are not effective hemostatic agents.

There are two major bodies of prior art concerned with bone hemostasis and bone healing, respectively. As discussed below, only products based upon plasticized non-absorbable waxes have generally been available to the surgeon for bone hemostasis. The few alternatives, such as makeshift devices using oxidized cellulose and electrocautery (discussed below), are not satisfactory.

The first body of art is directed specifically to bone waxes which are manually pressed into the pores of the bleeding bone surface, act as an effective mechanical tamponade, and prevent blood from escaping. Presently available bone waxes consist of mixtures of non-absorbable components such as bee's wax, paraffin, petrolatum, fatty ester plasticizers, and the like. These products must be warmed before use and become soft, kneadable and spreadable by the surgeon onto and into cut bone surfaces. Because available bone waxes are not absorbable and reside indefinitely where they are placed by the surgeon, they act as permanent physical barriers that inhibit osteogenesis, thereby preventing or slowing bone healing. In addition, such a site acts as a perpetual postoperative nidus for infection. If such infection does occur, it is usually chronic and difficult to treat using conventional anti-infective therapy and re-operation, to surgically excise the infected site, often becomes necessary. For these reasons, commercially available bone waxes do not enjoy widespread orthopedic use.

Other products or techniques used in this application include oxidized cellulose products indicated for soft tissue hemostasis, e.g., Surgicel®, which are absorbable and would not be expected to induce the complications cited above for bone wax. However, they are not effective hemostatic products for bone because of their inappropriate physical form (knitted fabric) and are too difficult to use effectively on cut bone because of lack of adherence within the bone pores.

The use of electrocautery, which thermally sears oozing blood vessels closed, is time-consuming and produces widespread tissue damage which may delay osteogenesis as well as allow soft tissue in-growth that interferes with normal bone union, presenting difficult problems for orthopedic surgeons in general and spine surgeons in particular.

Collagen in various forms, alone or in combination with fibrin and suspended in various delivery vehicles, has been proposed as a bone hemostatic agent but problems with, for example, storage stability, cohesiveness, and biocompatibility have prevented practical fruition.

The adaptation of synthetic absorbable polymers to this application has not succeeded, apparently because of technical difficulties in suitably formulating hydrolytically unstable synthetic absorbable polymers into practical products with reasonable package shelf life, useful handling properties and acceptable biocompatibility and absorption rates.

The second body of prior art primarily is concerned with bone healing and the treatment of bone defects. The bone healing prior art compilation primarily describes the development of biocompatible, absorbable vehicles to deliver and support processed particulate allogeneic bone as it is applied to defects such as excised cavities. These liquid or paste-like vehicles consist of a variety of polyhydroxy compounds, ester derivatives of polyols, hydrogels, and the like, sometimes containing additives to increase the viscosity of the vehicle (to retard dissipation of the vehicle and, thereby, extend the cohesiveness of the implanted mass) or factors to induce new bone growth. Anti-infective, anti-tumor and other additives also are described for these products. In no instances are these compositions indicated for, act as, or described in the art and claimed as bone hemostatic agents.

Thus, there remains a need in the art for a body absorbable hemostatic implant material that has suitable handling properties, biocompatibility and body absorption rates.

BRIEF SUMMARY OF THE INVENTION

The invention provides a composition having a waxy or putty-like consistency that preferably is capable of adhering to bone and functioning as an absorbable bone hemostatic agent. The composition comprises solid poloxamer having an average molecular weight of about 7,000 g/mol to about 15,000 g/mol, dextran having a molecular weight of about 40,000 Daltons to about 2,000,000 Daltons, optionally a fatty acid salt, and water.

Preferably the composition of the invention comprises (a) about 10% to about 75% (e.g., about 10% to about 65%), by weight of the composition, solid poloxamer having the molecular formula $HO(C_2H_4O)_a(C_3H_6O)_b(C_2H_4O)_aH$ having an average molecular weight of about 7,000 g/mol to about 15,000 g/mol, wherein the weight percent of ethylene oxide is 70 wt. % or more, based on the weight of the poloxamer, (b) about 1% to about 50%, by weight of the composition, dextran having a molecular weight of about 40,000 Daltons to about 2,000,000 Daltons; (c) about 10% to about 50%, by weight of the composition, water, and (d) about 0% to about 25%, by weight of the composition, finely powdered fatty acid salt. The amounts of (a)-(d) and any optional components that may be present desirably are sufficient to form a putty-like or wax-like consistency at ambient temperature.

The invention also provides a package comprising the composition of the invention, wherein the composition is amorphous or in a generally rounded form or in a generally parallelepiped form, wherein said composition is sealed in an aseptic barrier package, and is sterile or sterilizable.

The invention further provides a method for mechanically controlling the bleeding of bone which comprises applying an effective amount of the composition of the invention to the affected area.

DETAILED DESCRIPTION OF THE INVENTION

The composition of the present invention comprises a solid poloxamer, a high molecular weight dextran, water, and optionally a fatty acid salt. The composition of the present invention can have any suitable viscosity and cohesive strength and can have a waxy, or putty, or non-putty consistency. In many embodiments the composition of the invention has a putty-like consistency at ambient temperature. In one embodiment, the composition of the invention is a mechanically hemostatic tamponade useful in stopping the bleeding of bone by the application of the putty-like composition to the affected area. By "mechanically hemostatic tamponade" is meant that the composition functions by mechanically compressing the bleeding areas of the bone to arrest hemorrhaging as opposed to functioning by chemically hemostatic means, i.e., the arresting of hemorrhaging, in whole or in part, using a chemical means. In another embodiment, the composition of the invention, in addition to being mechanically hemostatic, is also osteogenic in that they contain an added ingredient, i.e., a bone growth-inducing material, to aid in the induction of bone growth.

The term "putty" is used herein as it is used in the art and is generally known to the skilled artisan. Dough (such as pastry dough), modeling clay, and glazier's putty of varying viscosities, depending on the indications and ultimate use, are examples of the consistency of a suitable product. Putties of various viscosities useable in the invention include those that are capable of adhering to bone. In general, putties which are soft, moldable, preferably non-elastic, cohesive mixtures prepared from a finely powdered substance intimately admixed with a liquid dispersing vehicle and having a shape which is capable of being deformed in any direction, are suitable consistencies for the putty-like compositions of the invention. As will be described later, however, compositions which have lower cohesive strengths than the putties described above, are within the scope of the invention, and may be used in specific applications in which the more viscous, higher cohesive strength putties are less suitable. For purposes of this invention, a major difference between putties of the invention and materials not considered to be putties (i.e. non-putties), but which are still within the scope of the invention, is that the non-putties have lower cohesive strengths than the cohesive strengths of the putty formulations. Individual non-putties of the invention are characterized by having the cohesive strength of creams, pastes, ointments, lotions, foams, gels, whipped egg whites, whipped cream, and the like. Preferably, the non-putties have only a fraction of the cohesive strength of putties of the invention, tending to be easily collapsible or easily torn apart under small stresses that would not, generally speaking, have the same effect on putties. The description which follows is given mainly in the context of the putties of the invention, it being understood, however, that if less cohesive strength materials are desired, the skilled artisan will simply make the appropriate changes in the proportions of components or add other substances to achieve the same purpose.

The poloxamer can be any suitable solid poloxamer. A poloxamer is a nonionic triblock copolymer containing a central hydrophobic chain of polyoxypropylene (i.e., poly(propylene oxide)) flanked by two hydrophilic chains of polyoxyethylene (i.e., poly(ethylene oxide)). The properties of the poloxamer are modified by customizing the lengths of the polymer blocks. Typically, the poloxamer used in the composition of the invention has an average molecular weight of about 7,000 g/mol to about 15,000 g/mol, preferably about 9,000 g/mol to about 13,000 g/mol, wherein the weight percent of ethylene oxide is 70 wt. % or more, based on the weight of the poloxamer. Desirably the solid poloxamer has the molecular formula $HO(C_2H_4O)_a(C_3H_6O)_b(C_2H_4O)_aH$, wherein a is 60 or greater and b is 25 or greater. Preferably, the solid poloxamer is selected from the group consisting of poloxamer 407 (a=101, b=56), poloxamer 338 (a=141, b=44), and poloxamer 188 (a=80, b=27). The amount of solid poloxamer can be any suitable amount, preferably about 10% to about 75%, or more preferably about 15% to about 65%, by weight of the composition.

The dextran can be any suitable dextran. Dextran is a branched polysaccharide comprising a plurality of glucose molecules, wherein the straight chain comprises α-1,6-glycosidic linkages between glucose molecules, and the branch chains begin from α-1,3-linkages of the glucose molecules. Typically the dextran is a high molecular weight dextran, e.g., dextran having a molecular weight of about 40,000 Daltons to about 2,000,000 Daltons. Preferably the dextran has a molecular weight of about 200,000 Daltons to about 1,000,000 Daltons, more preferably about 400,000 Daltons to about 600,000 Daltons (e.g., 500,000 Daltons). The amount of dextran can be any suitable amount. Typically, the composition of the invention comprises about 1% to about 50%, by weight of the composition, dextran. Preferably the composition of the invention comprises about 5% to about 40%. In some embodiments, it is desirable to include a relatively higher amount of poloxamer, for example about 40% to about 75%, in combination with a relatively lower amount of dextran, for example about 1% to about 20% (e.g., about 2% to about 15%).

The fatty acid salt is a salt of one or more saturated or unsaturated carboxylic acids containing about 6 to 22 carbon atoms in the chain, preferably 8 to 20 carbon atoms. More preferably, the fatty acid salt is a salt of a carboxylic acid containing 16-18 carbons in the chain. The salts can be any suitable salts, including calcium, magnesium, zinc, aluminum, lithium, and barium salts. Preferably, the fatty acid is selected from the group consisting of caprylic acid, capric acid, lauric acid, myristic acid, palmitic acid, stearic acid, arachidic acid, oleic acid, linoleic acid, and combinations thereof. More preferably, the fatty acid is selected from lauric, myristic, palmitic and stearic acids, with stearic being most preferred. In particularly preferred embodiments, the fatty acid salt is calcium palmitate, aluminum palmitate, calcium stearate, and aluminum stearate, or aluminum laurate, with calcium stearate being particularly preferred. Desirably the fatty acid salt is a finely divided material having an average particle size of 50 microns or less. Preferably the average particle size is between about 3 microns and 25 microns, more preferably between about 6 microns and 15 microns.

The composition of the invention optionally further comprises a calcium phosphate material, typically in the form of calcium phosphate ceramic granules. Suitable calcium phosphate materials include hydroxyapatite, tricalcium phosphate (e.g., α-TCP or β-TCP), tetracalcium phosphate, dicalcium phosphate, e.g., monetite and brushite, amorphous calcium phosphate, bioactive glasses composed of $SiO_2$, $Na_2O$, $CaO$ and $P_2O_5$, such as those composed of 35-60 mol. % $SiO_2$, 10-50 mol. % $CaO$, and 5-40 mol. % $Na_2O$; <35 mol. % $SiO_2$; >50 mol. % $SiO_2$, <10 mol. % $CaO$, and <35 mol. % $Na_2$; or >65 mol. % $SiO_2$, and wherein some $CaO$ is optionally replaced with $MgO$ or $CaF_2$, some $Na_2O$ is optionally replaced with $K_2O$, and/or some $B_2O_3$ or $Al_2O_3$ is optionally added, bioactive glass ceramics (e.g., apatite-wollastonite, and the like), carbonated apatites, ion-substituted calcium phosphates (e.g., calcium phosphate material in which the phosphate groups are selectively replaced with silicate or carbonate ions), cation-doped calcium phosphates (e.g., calcium phosphates or calcium carbonate phosphates doped with magnesium, zinc, yttrium, silver, strontium, etc.), and combinations thereof.

Desirably the calcium phosphate material is a finely divided material having an average particle size of 50 microns or less. Preferably the average particle size is between about 3 microns and 25 microns, more preferably between about 6 microns and 15 microns. The amount of calcium phosphate material can be any suitable amount. Preferably, when used, the amount of calcium phosphate material is about 1% to about 40%, or about 5% to about 25%, based on the weight of the composition.

In other embodiments, the invention optionally further comprises calcium sulfate (e.g., biphasic calcium sulfate) in an amount of about 5% to about 25%, based on the weight of the composition.

The composition of the invention comprises water or an aqueous solution. The presence of water aids in a variety of ways among which is changing the tactile quality of the composition. Suitable aqueous vehicles include water, saline, buffer solutions, body fluids (e.g., blood, serum, blood component concentrates), and the like. Desirably, the composition comprises a buffer solution that is isotonic and non-toxic such that it is suitable for use in medical applications. Typically the buffer solution has a pH between about 6.5 and 8.5, typically between 7 and 8 (e.g., 7.2 or 7.4). A preferred buffer solution for use in the composition of the invention is phosphate buffered saline, although borate buffered saline and tris buffered saline also can be used. Preferably the buffer solution comprises a chloride salt in combination with a phosphate, e.g., sodium chloride in combination with sodium phosphate, or potassium chloride in combination with potassium phosphate. Calcium or magnesium salts also can be used. One commonly used phosphate buffered saline is Dulbecco's phosphate buffered saline. The amount of the water or aqueous solution (e.g., buffer solution) can be any suitable amount. Preferably the composition of the invention comprises about 10% to about 50% water or aqueous solution, or preferably about 10% to about 50% phosphate buffered saline, based on the weight of the composition.

Optionally, the composition of the invention further comprises an additional ingredient selected from the group consisting of an absorbable colorant, an absorbable anti-infective agent, an absorbable blood clot-inducing agent, an absorbable anti-neoplastic agent, an absorbable analgesic, and an absorbable radiopaque agent. The colorant can be any suitable colorant. Suitable colorants include gentian violet, D&C Violet #2, and D&C Green #6. The anti-infective agent can be any suitable anti-infective agent. Suitable anti-infective agents include tetracycline, vancomycin, cephalosporins, aminoglycosides such as tobramycin and gentamicin, silver and its ionic forms, and antimicrobial peptides. The blood clot-inducing agent can be any suitable blood clot-inducing agent. Suitable blood-clot inducing agents include epinephrine, tannic acid, ferrous sulfate, and the double sulfates of a trivalent metal and a univalent metal such as potassium aluminum sulfate and ammonium aluminum sulfate. The anti-neoplastic agent can be any suitable anti-neoplastic agent. Suitable anti-neoplastic agents include methotrexate, cis-platinum, doxorubicin, radionuclides such as Strontium 89 and the like, and combinations thereof. The analgesic agent can be any suitable analgesic agent. Suitable analgesics include benzocaine, bupivacaine, dibucaine, lidocaine, mepivacaine, prilocaine, procaine, chloroprocaine, etidocaine, tetracaine, xylocaine, propivacaine, NSAIDs such as ibuprofen and aspirin and the COX-2 specific inhibitors such as rofecoxib and celecoxib, and combinations thereof. The radiopaque agent can be any suitable radiopaque agent. Typically the radiopaque agent is selected from the group consisting of iodo compounds, e.g., ethyl monoiodo state (Ethiodol, Savage Laboratories), and barium salts such as barium stearate.

The components described above, when added together in suitable proportions, yield useful, putty-like and non-putty like agents having, to varying degrees, many favorable characteristics. Various combinations of the components may require different times and temperatures in the preparation process in order for the putty-like characteristics to develop. For example, some materials such as finely divided hydroxyapatite may take longer than other components to achieve the putty-like state. Preferred compositions of the invention are as follows:

| Component | Composition A | Composition B | Composition C |
| --- | --- | --- | --- |
| Solid poloxamer (e.g., poloxamer 407) | 10%-30% | 45%-65% | 50%-75% |
| Dextran (e.g., 500 kD) | 30%-50% | 10%-15% | 1%-15% |
| Phosphate buffered saline | 30%-50% | 20%-35% | 15%-30% |
| Stearate salt (e.g., calcium stearate) | 0%-5% | 0%-10% | 5%-15% |
| Total | 100 | 100 | 100 |

In general, the putty-like compositions of the present invention are absorbable within a reasonable time, usually within 30 days although absorption times may be extended to several months or longer for some applications. They are moldable and shapeable by hand at ambient temperatures, handle well in presence of blood, and are washable with saline. They sometimes are tacky to the touch, but do not stick to any great degree to surgical gloves, wet or dry. They can be radiation sterilized when radiation-sensitive material such as DBM or certain antibiotics are not present.

The actual proportions of the materials selected will vary depending upon the materials themselves, the number of components used, and the use desired for the final putty composition. The user will be guided initially by the requirement for the desired viscosity, cohesive strength, and consistency to be obtained, i.e., compositions ranging from flowable liquid consistencies to consistencies of creams, pastes, ointments, gels, and the like to the more cohesive putty-like consistencies, while maintaining other characteristics desired in the ultimate use of the component.

The compositions described in this specification, when used surgically, must be sterile. All, except those noted below, are radiation sterilizable, using, for example, a standard cobalt-60 radiation source and a nominal dose of 25 kGy. Exceptions are formulations containing radiation-sensitive additives such as demineralized bone matrix, bone morphogenic protein, certain antibiotics, unsaturated molecules such as oleic acid and the like. When such materials are used, sterility may be achieved by radiation-sterilizing the bulk putty-like material and aseptically adding the sterile radiation-sensitive additive followed by aseptic packaging or by using e-beam or gamma radiation under controlled temperatures. The compositions of the invention can also optionally further comprise tocopherol acetate or radioprotectant agents which aid in preserving the biological activity during the sterilization process.

The composition of the invention may be sterile or sterilizable and may be packaged in several formats. The packages themselves may be sterile or sterilizable. The compositions may be packaged as an amorphous (i.e., shapeless or having no definite shape) material such as a paste, cream, or putty, or in the shape of its container. They may be shaped generally as a parallelepiped or as a generally rounded form, examples of the former being small brick-shapes or slabs (in the shape of a stick of chewing gum), and examples of the latter being cylindrical-shaped, egg-shaped, or spherical-shaped products. Alternatively, when the application permits and the viscosity is suitable, the product can be packaged in a syringe-like or plunger-assisted dispenser expressable or extrudable through an orifice of appropriate cross section and shape, for example, for use in minimally invasive percutaneous spinal techniques. A mechanical assist device similar to that used for caulking may be included. Another package contains the product in a squeezable, deformable tube such as a toothpaste-type tube or a collapsible tube such as those used in caulking applications, with an orifice shaped and sized to dispense any suitable shape onto the surface to be treated. The package may comprise an outer barrier as an overwrap, for example, a peelable blister pouch, to allow aseptic delivery of the package to the sterile field.

While the foregoing discussion has been presented largely in the context of materials having the consistency of a putty, in some applications it may be desired to have a relatively less viscous or less cohesive composition. For example, it may be desired to place the composition of the invention into a void in the bone (drilled or otherwise formed, e.g. hairline fractures) into which a putty of high viscosity can be applied only with difficulty. A less viscous form of the putty compositions of the invention would be a desirable alternative. All one needs to do is modify the proportions presented herein to allow for a higher liquid concentration or add a compatible liquid diluent to achieve this purpose. Using this approach, an injectable form of the material can be obtained as well. Other less cohesive strength, non-putty compositions, such as creams, ointments, gels, lotions, and the like previously referred to, may be prepared in the same manner. In other embodiments, it may be desired that the composition be prepared as a finely divided powder or powder aggregate that can be sprinkled in dry form onto a bleeding site to form a cohesive past upon contact with surgical fluids.

The present invention also contemplates methods of use of the compositions of the invention. For example, one embodiment is the method of mechanically controlling the bleeding of bone by the application of an effective amount of any of the compositions of the invention to bleeding bone, wherein the composition has a sufficiently dense consistency, such as in the putty compositions of the invention. In such a case, the composition is a mechanical hemostatic tamponade.

Another embodiment of the method of use of the invention is the method of chemically controlling the bleeding of bone by the application of an effective amount of any of the compositions of the invention, wherein the composition contains a blood clot-inducing agent as heretofore set forth. In the case of putties, the composition is a chemical hemostatic tamponade. Mechanical hemostatic tamponades of the invention which also comprise a clot-inducing agent will act as both a mechanical hemostat and a chemical hemostat.

Another method of the invention is the method for inducing the growth of bone in a bone defect by applying an effective amount of any composition of the invention containing a bone growth-inducing agent, to the affected area of bone, especially when the composition includes a bone growth-inducing material such as a calcium phosphate material.

Another method is the method for treating an infection in or around a bone by applying an effective amount of any composition of the invention containing an anti-infective agent, to the affected area of bone to be treated.

Another method is the method for destroying cancer cells in or around a bone by applying an effective amount of any composition of the invention containing an anti-neoplastic agent, to the affected area of bone which contains such cells.

Another method is the method for reducing pain from an area in or around a bone by applying an effective amount of any composition of the invention containing an analgesic agent, to the affected area.

Another method is the method for controlling inflammation in or around a bone by applying an effective amount of any composition of the invention containing an anti-inflammatory agent, to the affected area.

Another method is the method for assessing the status of an area in bone to which an implant has been applied by applying an effective amount of any composition of the invention containing a radiopaque agent, to the affected area and thereafter radiographically visualizing the area and making a determination of the status of the area.

The following examples further illustrate the invention but, of course, should not be construed as in any way limiting its scope.

Example 1

In this example and in all subsequent examples, unless otherwise indicated, the compositions were prepared by mechanical blending of all dry ingredients first and thereafter adding gradually any liquid components.

| Component | Composition A | Composition B | Composition C |
|---|---|---|---|
| Poloxamer 407 | 20% | 55% | 60.83% |
| Dextran 500 kD | 40% | 12.5% | 6.75% |
| Dulbecco's phosphate buffered saline | 40% | 27.5% | 23.75% |
| Calcium stearate | 0% | 5% | 9.17% |

The compositions were "worked" with a spatula at room temperature until the desired consistency was obtained. The compositions of the invention A, B and C yielded a putty-like mass.

Example 2

The in vivo response to each of the hemostatic compositions A-C of the invention described in Example 1 was evaluated in a cancellous defect in young (10 week old) rabbits at 5 and 14 days postoperatively.

Three animals per time point (6 sites) were implanted with one each of respective Compositions A-C with contralateral control of a clinically available water soluble bone hemostat predicate (Ostene, Apatech Ltd., Baxter Healthcare Corp.). One animal per time point (2 sites) was used for sham surgery (empty) for inflammatory comparison.

A 3×10 mm drill hole defect was created in the left and right distal femurs of 8 New Zealand White Rabbits. Compositions (i.e., Compositions A, B, C, Ostene, or none (empty) according to the table below) were carefully placed in the defect to the height of the original cortex and the skin was closed using 3-0 Polysorb. The rabbits were given post-operative analgesia and returned to their cages where they were free to mobilize and weight-bear immediately post-operatively as tolerated. The rabbits were monitored daily following surgery.

| Rabbit | Left Femur | Right Femur | Time Point |
|---|---|---|---|
| 1 | Composition A | Ostene | 14 days |
| 2 | Ostene | Composition B | 14 days |
| 3 | Composition C | Ostene | 14 days |
| 4 | Empty | Ostene | 14 days |
| 5 | Composition A | Ostene | 5 days |
| 6 | Ostene | Composition B | 5 days |
| 7 | Composition C | Ostene | 5 days |
| 8 | Empty | Ostene | 5 days |

Each of the Compositions A-C handled well and was easily placed into the defect. Hemostasis was achieved immediately upon filling the defects with each of the Compositions A-C, while the empty sham control sites bled for some time after defect creation and hemostasis was achieved only after 3-4 minutes with a sponge.

No post-operative complications were encountered and no adverse reactions were noted in any animal at any time point. Faxitron radiographs in the anteroposterior and lateral planes taken at 5 and 14 days post-operatively revealed no abnormal bone reactions or bony resorption of post-operative fractures. Micro computed tomography confirmed the radiographic findings in terms of site placement and no evidence of adverse inflammatory response in any animal at 5 or 14 days. Bone healing was not evident in any animal at 5 days, but progressed in each animal with time by 14 days. No abnormalities were noted on the distant organs (heart, liver, kidney, spleen, and lungs) when examined macroscopically or microscopically at the time of harvest (5 or 14 days post-operatively).

Histology of the soft tissue overlying the defect at 5 days revealed the presence of normal inflammatory and granuloma reactions in all sites including those from the empty defect. The granuloma reactions were consistently the surgically created defect. Histology of the soft tissue overlying the defect at 14 days revealed no major differences for Compositions A-C compared to the predicate (Ostene).

At day 5 postoperatively, the bone defects were filled with soft tissues and haematoma surrounding the implanted materials. The cell population included red blood cells, white blood cells, fibroblasts, monocytes, macrophages, giant cells, osteoblasts, osteoblast progenitors and osteoclasts. The soft tissues penetrated into the implant materials with new blood vessel formation in the bone defect site. Compositions A-C presented similar features in terms of cellular population. Compositions B and C had a similar response while Composition A appeared to have a lower overall cellular infiltration. The cell population and amount of fibrous tissue was similar to the predicate material (Ostene). The empty defect showed a similar cell population as Compositions A-C and the predicate (Ostene) but with fewer white blood cells and less granuloma reaction.

At day 14 postoperatively, the predicate (Ostene) treated defects had fibrous soft tissues as well as some new woven bone. The soft tissue component included fibroblasts, monocytes, white blood cells (neutrophils and lymphocytes), and some macrophages and giant cells present. The defects filled with Compositions A-C had a similar response to the predicate (Ostene) in terms of new woven bone as well as the presence of fibrous tissue and cellular components. The histology of the empty defect at day 14 revealed the presence of new woven bone.

The amount of new bone in the defects and other tissue was evaluated by histomorphometry (see table below). Residual material was not able to be differentiated at 5 days and could not be found at 14 days, reflecting in part the in vivo resorption of the material as well as the histology processing fluids that could potentially remove remaining material.

| Rabbit | Composition | Time Point | New Bone | Other Tissue |
|---|---|---|---|---|
| 1-left | Composition A | 14 days | 0.12 | 0.88 |
| 1-right | Ostene | 14 days | 0.16 | 0.84 |
| 2-left | Ostene | 14 days | 0.41 | 0.59 |
| 2-right | Composition B | 14 days | 0.20 | 0.80 |
| 3-left | Composition C | 14 days | 0.33 | 0.67 |
| 3-right | Ostene | 14 days | 0.16 | 0.84 |
| 4-left | Empty | 14 days | 0.39 | 0.61 |
| 4-right | Ostene | 14 days | 0.51 | 0.49 |
| 5-left | Composition A | 5 days | 0.00 | 1.00 |
| 5-right | Ostene | 5 days | 0.16 | 0.84 |
| 6-left | Ostene | 5 days | 0.03 | 0.97 |
| 6-right | Composition B | 5 days | 0.00 | 1.00 |
| 7-left | Composition C | 5 days | 0.00 | 1.00 |
| 7-right | Ostene | 5 days | 0.03 | 0.97 |
| 8-left | Empty | 5 days | 0.27 | 0.73 |
| 8-right | Ostene | 5 days | 0.00 | 1.00 |

Each of the compositions A, B and C of the invention demonstrated an acceptable inflammatory response and no bony reactions relative to an empty defect and a predicate material (Ostene). This example demonstrates that each of the compositions A-C of the invention have an acceptable in vivo response.

Example 3

The hemostatic properties of each of the hemostatic compositions A-C of the invention described in Example 1 was evaluated in cortical defects located on the ribs of a pig.

The ribs of a pig were exposed and 1.5 cm×1.5 cm cortical bone defects were created using a 4 mm burr attached to a nitrogen powered handpiece. Cortical bone was removed from the defect site until widespread punctuate bleeding to brisk oozing was observed. Once bleeding was observed, Compositions A, B, and C were applied to the defects until hemostasis was achieved. The compositions were removed from the packaging and then manipulated with dry gloves to warm the material to make it soft and malleable. Once the desired consistency was reached, the softened articles were pressed into the bleeding bone defect site using a finger and the defect was filled. The application was accomplished by either pressing the compositions into the defect site or smearing the compositions into the defect site.

Once hemostasis was determined to be adequate after application, observations for bleeding were performed at 5 and 10 minutes. After 10 minutes, the sites were observed every 30 minutes until composition failure or 6 hours after the initial defect. A similar defect was created initially and at the end of the procedure to act as a control. The control defect was observed at 5 and 10 minutes for bleeding, and at 10 minutes, bone wax (Ethicon) was applied to create hemostasis. A summary of the defect locations and treatment is provided in the table below.

| Rib | Anatomical Location (cranial to caudal) | Dorsal Rib Defect | Middle Rib Defect | Ventral Rib Defect |
| --- | --- | --- | --- | --- |
| 1 | 4 | Untreated Control | Composition A | Composition B |
| 2 | 5 | Composition C | Composition B | Composition A |
| 3 | 6 | Composition A | Composition C | Composition B |
| 4 | 7 | Composition B | Composition A | Composition C |
| 5 | 8 | Composition C | Untreated Control | None |

Composition A was superior for application using the "press on" technique, while Compositions B and C were difficult to conform to the defect. The press on technique created considerable excess composition, which made evaluation of rebleeding difficult. A summary of the results using the press on technique are summarized below.

| | Composition | | | | |
| --- | --- | --- | --- | --- | --- |
| | A | A | B | B | C |
| Time to achieve hemostasis (seconds) | 7 | 23 | 25 | 28 | 60 |
| Rib Number | 1 | 3 | 1 | 3 | 3 |
| Time of rebleed (h) | 5 min | 1 | 2 | 0.5 | 0.5 |

Compositions B and C were best in terms of the "smear" technique, while Composition A was the worst for application with slippery properties and sticking of the composition to gloves during application. All of the Compositions A, B and C applied with the smear technique maintained hemostasis for greater than 1 hour. A summary of the results using the smear technique are summarized below.

| Composition | A | A | B | B | C | C |
| --- | --- | --- | --- | --- | --- | --- |
| Time to achieve hemostasis (seconds) | 5 | 22 | 10 | 20 | 57 | 11 |
| Rib Number | 2 | 4 | 2 | 4 | 2 | 4 |
| Time of rebleed (h) | 2 | 2 | 5 | 3.5 | Not observed (6 h) | 1.5 |

This example demonstrates that all of the compositions A-C of the invention have suitable hemostatic properties. Composition A was superior for application using the "press on" technique, while Compositions B and C were superior for the "smear" technique. All of Compositions A-C applied with the smear technique maintained hemostasis for at least 1 hour.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A putty composition consisting of:
    (a) about 55%, by weight of the composition, poloxamer 407;
    (b) about 12.5%, by weight of the composition, dextran having a molecular weight of about 500,000 Daltons;
    (c) about 27.5%, by weight of the composition, phosphate buffered saline, and
    (d) about 5%, by weight of the composition, calcium stearate,
    wherein the putty composition is moldable at ambient temperature and non-elastic.

2. A putty composition consisting of:
(a) about 60.83%, by weight of the composition, poloxamer 407;
(b) about 6.25%, by weight of the composition, dextran having a molecular weight of about 500,000 Daltons;
(c) about 23.75%, by weight of the composition, phosphate buffered saline, and
(d) about 9.17%, by weight of the composition, calcium stearate,
wherein the putty composition is moldable at ambient temperature and non-elastic.

* * * * *